US00PP23496P2

(12) United States Plant Patent
Moy et al.

(10) Patent No.: US PP23,496 P2
(45) Date of Patent: Mar. 26, 2013

(54) ***CITRUS* TREE NAMED 'GREMOY47'**

(50) Latin Name: *Citrus reticulata*
Varietal Denomination: Gremoy47

(75) Inventors: Ying Doon Moy, Spring, TX (US); Larry Stein, Uvalde, TX (US)

(73) Assignee: Green Leaf Nursery Co., Park Hill, OK (US)

( * ) Notice: Subject to any disclaimer, the term of this patent is extended or adjusted under 35 U.S.C. 154(b) by 117 days.

(21) Appl. No.: 13/065,236

(22) Filed: Mar. 17, 2011

(51) Int. Cl.
*A01H 5/00* (2006.01)

(52) U.S. Cl. ..... Plt./201; Plt./202

(58) Field of Classification Search ..... Plt./201, Plt./202
See application file for complete search history.

*Primary Examiner* — Kent L Bell
(74) *Attorney, Agent, or Firm* — Penny J. Aguirre

(57) ABSTRACT

A new cultivar of *Citrus* tree, 'Gremoy47', that is characterized by its cold hardiness and its fruit with few seeds, an easy to peel skin, and a sweet, tart flavor.

2 Drawing Sheets

Botanical classification: *Citrus reticulata.*
Varietal denomination: 'Gremoy47'.

BACKGROUND OF THE INVENTION

The present invention relates to a new and distinct cultivar of satsuma mandarin tree, botanically known as *Citrus reticulata* 'Gremoy47', referred to hereafter by its cultivar name, 'Gremoy47'.

The new cultivar was derived from a controlled breeding program conducted by the Inventors in San Antonio, Tex., U.S.A. The overall purpose of the breeding program is the creation of Satsuma (mandarins) and tangerine hybrids that exhibit the fruit quality of Satsumas and the cold tolerance of select cold hardy tangerine varieties.

'Gremoy47' was selected by the Inventors in 2005 as a single unique tree that resulted from embryo rescue of a seed obtained from a cross made by the Inventors in 1998 between *Citrus reticulata* 'Changsha' (not patented), a tangerine, and an unnamed seedling of *Citrus reticulata* var. *unshui* (syn, *Citrus unshui*, not patented), a manderin, as the male parent.

Asexual reproduction of the new cultivar was first accomplished by stem cuttings in San Antonio, Tex. in 2005 by one of the Inventors. It has been determined that the characteristics of this cultivar are stable and are reproduced true to type in successive generations.

SUMMARY OF THE INVENTION

The following traits have been repeatedly observed and represent the characteristics of the new cultivar of *Citrus.*

1. 'Gremoy47' has been observed to be cold hardy to at least 12° F. (defoliation occurs at temperatures below about 15° F., foliage is evergreen above about 15° F.)
2. 'Gremoy47' exhibits fruit that is similar in quality to high quality Satsuma type *Citrus* trees with few seeds present (0 to 4 per fruit).
3. 'Gremoy47' exhibits fruit with an easy to peel skin.
4. 'Gremoy47' exhibits fruit with a sweet and tart flavor.

'Gremoy47' is readily distinguished from its female parent plant, 'Changsha'. Although 'Changsha' exhibits slightly better cold hardiness, the fruit of 'Gremoy47' is much improved, as the fruit of 'Changsha' is less flavorful, has abundant seeds, and more difficult to peel. In comparison to the male parent, a satsuma type seedling selection, 'Gremoy47' is more cold hardy and the flavor of 'Gremoy47' fruit is more tart. 'Gremoy47' can be compared to *Citrus retuculata* var. *unshiu* 'Seto' (not patented). 'Seto' differs from 'Gremoy47' in being less cold hardy.

BRIEF DESCRIPTION OF THE DRAWINGS

The accompanying color photographs illustrate the distinguishing characteristics of the new cultivar 'Gremoy47'. The photographs were taken of the tree and fruit of an 8 year-old tree as grown in San Antonio, Tex.

Figure 1:
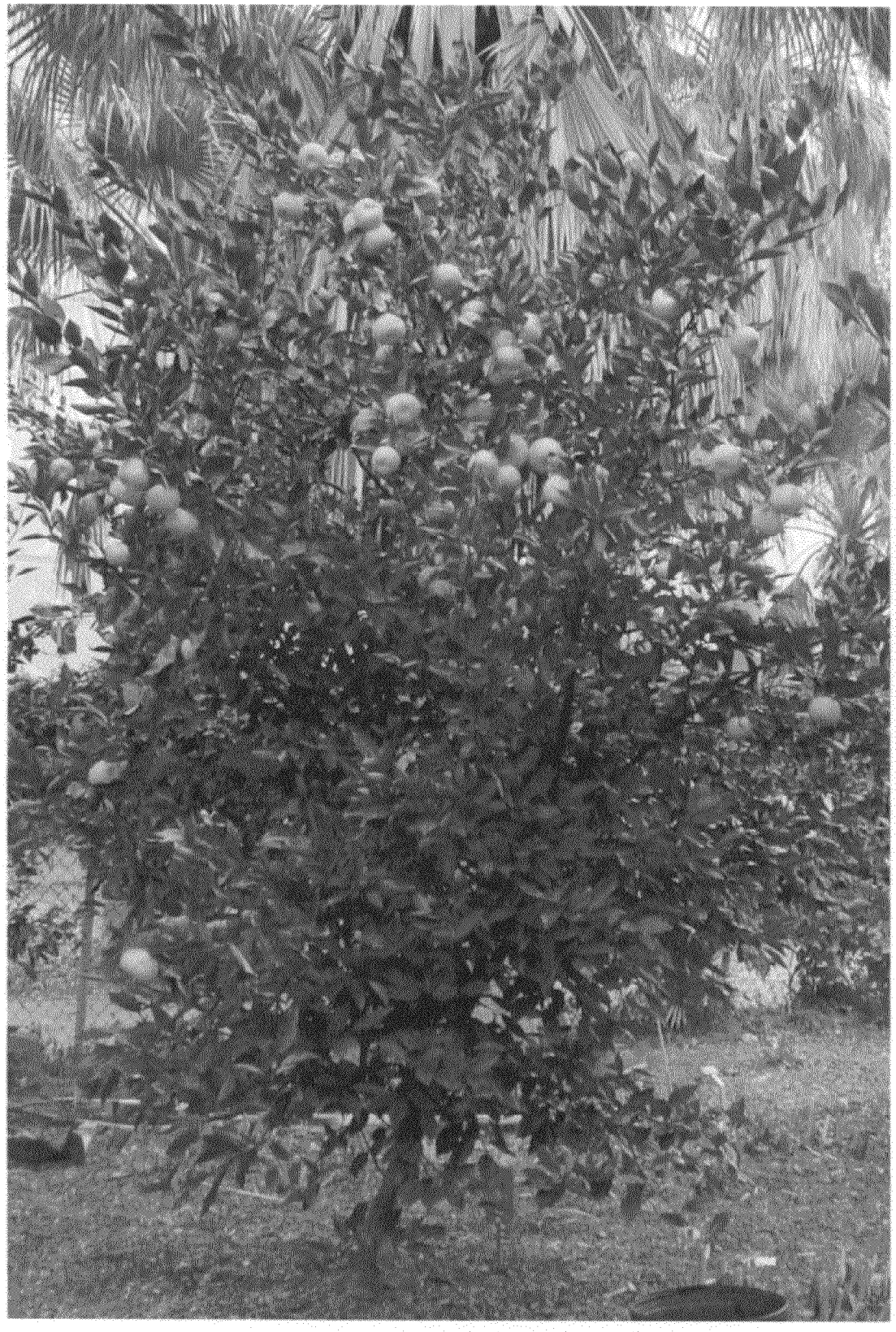
FIG. 1 shows a tree of 'Gremoy47' in fruit.
Figure 2:
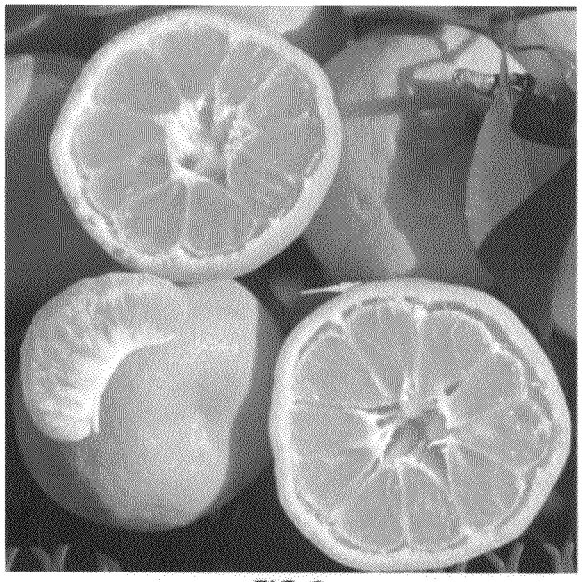
FIG. 2 shows a cross section and a section of the fruit of 'Gremoy47'.
Figure 3:
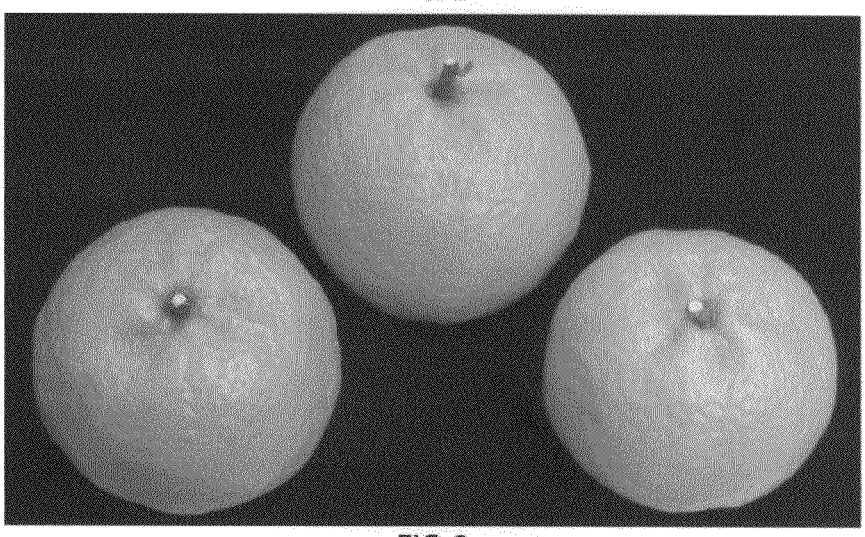
FIG. 3 shows three entire fruits of 'Gremoy47'.
Figure 4:
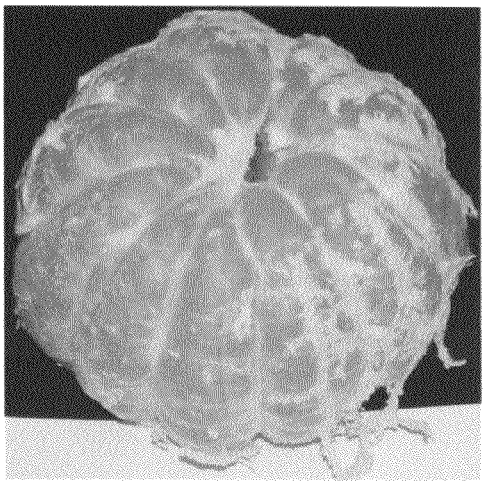
FIG. 4 shows a peeled fruit of 'Gremoy47'.

The colors in the photographs are as close as possible with digital photography techniques available, the color values cited in the detailed botanical description accurately describe the colors of the *Citrus.*

DETAILED BOTANICAL DESCRIPTION

The following is a detailed description of four year-old plants (from cuttings) of 'Gremoy47' as grown in 30-gallon containers in El Campo, Tex. with measurements of mature trees taken from plants grown in a trial plot for a period of 8 years. The phenotype may vary somewhat with variations in temperature, day length, light intensity, soil types and water and fertility levels, without, however, any variance in the genotype. The color codes numbers refer to The 2007 Royal Horticultural Society's Colour Chart, London, England; except when general color terms of ordinary dictionary significance are used.

Tree description:

*Tree type.*—Sub-tropical shrub.

*Tree habit.*—Broad, upright growth habit.

*Tree size.*—Reaches about 8 to 10 feet in height and 8 feet in width.

*Trunk description*.—Multi-stemmed from base, a seven year-old plant has an average of 8 main stems from base; an average of 4.5 cm in diameter observed 30 cm above soil level.

*Growth rate*.—Moderate.

*Diseases and pests*.—No unique susceptibility or resistance has been observed when grown with other satsumas/tangerines cultivars.

*Hardiness*.—At least U.S.D.A. Zone 8A, has been found to be hardy to at least 12° F. and remains evergreen to about 15° F.

*Propagation*.—Stem cuttings or budding onto rootstock.

*Branching habit*.—Freely branched, branching at approximately 45° from main stems.

*Branch diameter*.—Average of 6 cm.

*Branch surface*.—Smooth on new growth and becoming sandpaper-like with irregular fine ridges in 3 to 4 years.

*Internode length*.—Average of 2.5 cm.

*Branch frequency*.—Moderate.

*Branch strength*.—Strong.

*Bark color of tree trunk*.—N137A throughout, covered in a thin layer of bark 196D in color, thickened bark turns 203B in roughest and mature sections, slightly rough to the touch.

Description of mature shoots:

*Stem appearance*.—Young stems irregularly angular in shape, filling out to round with age.

*Shoot texture*.—Smooth when young and sandpaper-like with irregular fine ridges after 3 years.

*Shoot internode length*.—Average of 2.5 cm.

*Stem strength*.—Strong and flexible, not brittle.

*Thickness of shoot at center of middle internode*.—Variable with age.

*Shine of bark*.—Juvenile; smooth, matte finish.

*Stem color*.—177A.

*Shoot angle*.—Approximately 45°.

Description of growing shoots:

*Color of shoot*.—Emerging N144C, mature N137A.

*Surface*.—Sparsely pubescent.

Leaf description:

*Leaf orientation*.—Upward to outward.

*Leaf division*.—Simple.

*Leaf shape*.—Elliptic to ovate.

*Leaf blade size*.—Average of 12.2 cm in length and 7.2 cm in width.

*Leaf apex*.—Acuminate to cuspidate, apical margin minutely cleft.

*Leaf base*.—Rounded to attenuate.

*Leaf surface*.—Slightly glaucous to glossy, speckled with minutely translucent glands.

*Leaf texture*.—Thick and leathery.

*Leaf margin*.—Finely crenulate to finely serrulate, with minute translucent glands.

*Leaf color*.—Upper surface emerging leaves 144A, mature leaves N137A; lower surface emerging leaves 144B, mature leaves 146B.

*Leaf venation*.—Pinnate, upper surface 137C in color, lower surface prominently raised main vein and slightly raised lateral veins, 143C in color.

*Petiole*.—Winged, average of 2.0 cm in length, 2 mm in diameter, wings 0.5 cm in width, 137B in color.

*Durability of foliage to stress*.—Returns from wilt with no damage, resists wind and desiccation.

*Thorns*.—Infrequent, at base of lateral branches opposite petiole when present, 0.3 to 3 cm in length, 0.5 to 2 mm in diameter, 137B at base, 144B towards apex.

Flower description:

*Flowering period*.—About 2 weeks in spring in Texas, timing is temperature and location dependent, in upper coastal Texas, first bloom generally occurs in mid March.

*Number of flowers*.—1 to 2 per node.

*Inflorescence type*.—Single flowers.

*Flower buds*.—Globose in shape, 5 parted, NN155C in color, 1 to 1.3 cm in length and 7 mm in diameter.

*Flower size*.—3 to 3.5 cm in diameter, an average of 8 mm in depth.

*Flower fragrance*.—Mildly sweet, gardenia-like.

*Flower aspect*.—Upright and outward.

*Petals*.—5 per flower, un-fused, elliptic in shape, acute apex, truncate base, entire margin, about 1.8 cm in length and 7 mm in width, color of upper and lower surface NN155C, surface is satiny and glabrous, thick substance.

*Sepals*.—5, fused with an small acute apex on each, 144C in color on upper and lower surface, waxy surface, triangular in shape, entire margin, curled inward around nectary, fused base, calyx is 4 mm in diameter, 4.5 mm in length and circular in shape and tapering to a small tube about 3 mm in length and width.

*Pedicel*.—144A in color, average of 1.5 mm in length and 1.5 mm in width, waxy surface.

*Pistil*.—1, 6 mm in length, style is 145B in color and 4 mm in length, stigma is 151D in color and globose in shape, ovary is globose in shape, inferior, waxy in appearance and 144A in color, nectary is disk-shaped, 3 to 4 mm in diameter, 1 mm in depth, 150D in color, waxy surface.

*Stamens*.—16 to 18 per flower, filaments are fused into upright ring, 155C in color, and 8 to 10 mm in length, anther is oblong in shape, 7A in color and 1.5 to 2 mm in length, pollen is dry and powdery and 21A in color.

Fruit description:

*Fruit harvest*.—First picking is generally mid November if temperature have been cool for sufficient sugar development, last picking is generally late December just prior to freezing temperatures.

*Fruit type*.—Hesperidium, average of 10 segments.

*Fruit size*.—Average of 7.5 cm in diameter and 5 cm in height.

*Fruit weight*.—Average of 160 g per fruit.

*Fruit aroma*.—Skin when peeling; strong citrus oil, flesh; orange.

*Fruit shape*.—Oblate.

*Fruit symmetry*.—Asymmetrical top to bottom hemisphere, Nearly symmetrical right to left hemisphere.

*Fruit flavor*.—Sweet and tart.

*Fruit skin*.—Easy to peel, 0.5 cm in thickness, outer surface; rugulose, slightly glossy, 25A, inner surface; fibrous NN155C.

*Color of outer surface*.—25A.

*Color of flesh*.—N24A with carpel partitions 155B in color.

*Color of albedo*.—19C.

*Navel presence*.—None.

*Skin (rind)*.—Easy to peel, 0.5 cm in thickness, outer surface; rugulose, slightly glossy, 23A, inner surface; fibrous NN155C.

*Fruit segments*.—10, kidney-shaped, an average of 5 cm in length and 1.5 cm in width.

*Fruit set*.—Medium, heavily dependent on early spring weather during bloom.

*Seed*.—0 to 1 seeds per section, 0 to 2 seeds per fruit.

*Texture of flesh*.—Juicy, glossy, slight indentations.

*Cropping frequency*.—Annually.

*Fruit brix*.—12 from refractometer.

*Juice production*.—Average of 100 ml per fruit.

*Fruit keeping quality*.—About 4 weeks at room temperatures before rind begins to mummify and fruit volume begins to shrink from dehydration, 6 to 8 weeks if refrigerated with humidity control.

*Fruit shipping quality*.—Thin skinned, soft and fragile; packing materials must be used to provide structural support and even weight distribution.

*Fruit use*.—Primarily for fresh consumption but may be juiced.

It is claimed:

1. A new and distinct variety of orange tree named 'Gremoy47' as described and illustrated herein.

* * * * *